United States Patent [19]

Wallace

[11] Patent Number: 5,824,476
[45] Date of Patent: *Oct. 20, 1998

[54] COMPETITIVE HYBRIDIZATION TECHNIQUE

[75] Inventor: R. Bruce Wallace, S. Pasadena, Calif.

[73] Assignee: City of Hope, Duarte, Calif.

[*] Notice: The term of this patent shall not extend beyond the expiration date of Pat. No. 5,582,970.

[21] Appl. No.: 607,425

[22] Filed: Feb. 28, 1996

Related U.S. Application Data

[63] Continuation of Ser. No. 71,210, Jul. 8, 1997, Pat. No. 5,582,970.

[51] Int. Cl.⁶ ............................. C12Q 1/68; C07H 21/02; C07H 21/04
[52] U.S. Cl. ............................. 435/6; 536/24.3; 935/77; 935/78
[58] Field of Search ............................. 435/6; 536/24.3; 935/77, 78

[56] References Cited

U.S. PATENT DOCUMENTS 4,683,194  7/1987  Saiki et al. .................................. 435/6

FOREIGN PATENT DOCUMENTS 0130515  1/1985  European Pat. Off. ................... 435/6
8809385  12/1988  WIPO ........................................ 435/6

OTHER PUBLICATIONS

Lathe, R., *J. Mol. Biol., 183*:1–12 1985.
Nozari et al., *Gene, 43*:23–28 (1986).
Oostra et al., *Anal. Biochem, 74*:496–502 (1976).
Orkin et al., *J. Clin. Invest., 71*:775–779 (1983).
Alonso et al., *Exp. Cell Res., 85*: 383–390 (1974).
Maniatis et al., *Molec. Cloning:A Lab. Man.*, Cold Spring Harbor, 1982.
Conner et al., *Proc. Natl. Acad. Sci. USA*, 80:278–282 (1983).
Studencki & Wallace, DNA 3(1):7–15 (1984).

*Primary Examiner*—Stephanie W. Zitomer
*Attorney, Agent, or Firm*—Rothwell, Figg, Ernst & Kurz

[57] ABSTRACT

Discrimination between RNAs which differ by as little as a single nucleotide is accomplished by having an excess of unlabeled non-complementary oligonucleotide present during hybridization with a labeled complementary nucleotide. The non-complementary oligonucleotide blocks hybridization of the labeled complementary oligonucleotide sequence without affecting hybridization of the labeled complementary oligonucleotide to the complementary sequence. The label may be an isotope, a fluorescent group or of any other type. The technique permits examination of the transcription of highly related allelic and non-allelic genes present in the same cell and the quantification of such transcripts by use of appropriate internal control. The technique is also useful in oligonucleotide hybridization to DNA sequences which differ only by a single nucleotide.

10 Claims, 1 Drawing Sheet

5,824,476

COMPETITIVE HYBRIDIZATION TECHNIQUE

This is a continuation of application Ser. No. 07/071,210, filed Jul. 8, 1987 issued Dec. 10, 1996 as U.S. Pat. No. 5,582,970.

This invention provides a technique for discriminating between RNAs and DNAs which differ by as little as a single nucleotide. The technique is fully described in Nozari, Rahbar and Wallace, "Discrimination among the transcripts of the allelic human β-globin genes $β^A$, $β^S$ and $β^C$ using oligodeoxynucleotide hybridization probes," *Gene*, 43:23–28 (1986).

BACKGROUND OF THE INVENTION

The ability to discriminate between two genes that differ by only a single base pair has led to important applications, particularly in the diagnosis of certain human genetic diseases as well as to the screening of mutations created by site-directed mutagenesis. The most general approach to this discrimination has been through the use of specific synthetic oligo hybridization probes. Oligo:DNA duplexes containing single base pair mismatches are significantly less stable than those which are perfectly base-paired. Under appropriate conditions, oligo probes will only hybridize to their cognate sequence and not to a sequence containing one or more non-complementary nucleotide. Thus, oligo hybridization can be used to determine the sequence of a short region of a DNA molecule.

Until recently, it has not been possible to discriminate between RNA molecules which differ by only a single nucleotide. Although oligo probes have been used to discriminate between highly related RNAs, never have single nucleotide differences been probed.

It has been shown that G:T mismatches in oligo:DNA duplexes are less destabilizing than other mismatches. Similarly, G:U mismatches in RNA:RNA duplexes are more stable than other mismatches. To optimally discriminate two genes which differ by a single transition mutation, oligo probes can be synthesized such that they form an A:C mismatch with the DNA of the non-complementary allele. Due to the fact that RNA is single stranded, it is not always possible to avoid an oligo probe forming a G:T or G:U mismatch with a non-complementary RNA when hybridizing oligo probes to two RNA molecules which differ by a single nucleotide. To discriminate the two RNAs on the basis of oligo hybridization, one must attempt to optimize the destabilizing effect of the mismatch formed.

SUMMARY OF THE INVENTION

Discrimination between RNAs which differ by as little as a single nucleotide is accomplished by having an excess of unlabeled non-complementary oligonucleotide present during hybridization with a labeled complementary nucleotide. The non-complementary oligonucleotide blocks hybridization of the labeled complementary oligonucleotide sequence without affecting hybridization of the labeled complementary oligonucleotide to the complementary sequence. The label may be an isotope, a fluorescent group or of any other type. The technique permits examination of the transcription of highly related allelic and non-allelic genes present in the same cell and the quantification of such transcripts by use of appropriate internal control. The technique is also useful in oligonucleotide hybridization to DNA sequences which differ only by a single nucleotide.

Figure 1:
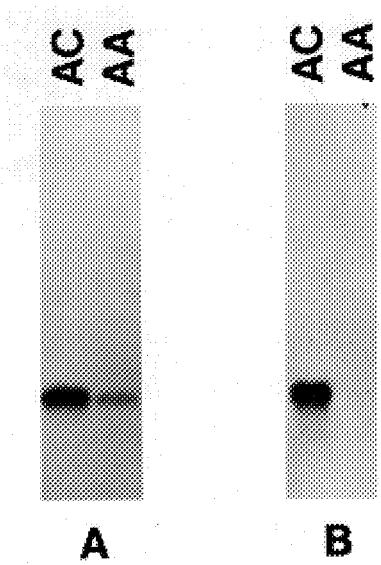
FIGS. 1(A and B) Effect of competitor oligo on the hybridization specificity of oligo probes to β-globin mRNA. RNA was prepared from blood cells of individuals which are either homozygous for the normal β-globin gene (AA) or heterozygous for the normal and $β^C$-globin genes (AC). The RNA was denatured, subjected to electrophoresis on an agarose gel and transferred to a GeneScreen filter. The filter was hybridized with Hβ19C' [$^{32}$P]probe in the absence (FIG. 1A) or presence (FIG. 1B) of a 10-fold molar excess of unlabeled Hβ19A'. The hybridizing band was the same mobility as commercially available rabbit globin mRNA (Bethesda Research Laboratories).

Hybridized with Hβ19A'[$^{32}$P]probe in the absence of unlabeled non-complementary-oligo (non-c-oligo).

Hybridized with Hβ19S'[$^{32}$P]probe in the presence of unlabeled Hβ19A' as the non-c-oligo.

Hybridized with Hβ19C'[$^{32}$P]probe in the presence of unlabeled Hβ19A' as the non-c-oligo.

Hybridized probe was removed between hybridizations by washing the blot in 1×SSC at 50° C. for 15 min., then in 0.1×SSC at 50° C. for 15 min., and finally in 0.01×SSC at 68° for 30 min. The filter was autoradiographed overnight to check that hybridized probe was completely removed.

DETAILED DESCRIPTION OF THE INVENTION

RNA Preparation—RNA was prepared from 20 ml of heparinized blood obtained from various individuals of differing β-globin genotypes. Red cells were lysed by resuspending the washed cell pellet in 0.144M $NH_4Cl$, 3 mM dithiothreitol (DDT), followed by the addition of 0.1 vol. of 0.01M $NH_4HCO_3$. To the lysate is added 0.1 vol. of 1.5M sucrose, 0.5M KCl and 0.5% sodium dodecyl sulfate (SDS), and the solution was centrifuged at 3000×g for 20 min. at 4° C. The ribonucleoprotein was recovered from the supernatant by precipitation at pH 5 using 10% acetic acid followed by centrifugation at 3000×g for 20 min. at 4° C. The pellet was dissolved in 0.1M Tris-HCl pH 9, 0.1M NaCl, 1 mM EDTA and 0.1% SDS, and extracted first with phenol-chloroform and then with chloroform-isoamyl alcohol followed by ethanol precipitation.

Oligo Probe Design—The sequences of the oligos used in this study are given in Table I.

TABLE I

Oligonucleotide Probes for the Discrimination of β$^A$, β$^S$ and β$^C$ mRNA

| β-Globin | aa No. | 3 | 4 | 5 | 6$^{a/}$ | 7 | 8 | 9 | 10 | Mismatches with β$^A$ | Mismatches with β$^S$ | Mismatches with β$^C$ |
|---|---|---|---|---|---|---|---|---|---|---|---|---|
| β$^A$ | ... |  | Leu | Thr | Pro | Glu | Glu | Lys | Ser | Ala ... |  |  |  |
| mRNA | 5' | CUG | ACU | CCU | GAG | GAG | AAG | UCU | GCC3' |  |  |  |
| H 19A' |  | 3' | GA | GGA | CTC | CTC | TTC | AGA | CG 5' | — | T:U | C:A |
| β$^S$ | ... |  | Leu | Thr | Pro | Val | Glu | Lys | Ser | Ala ... |  |  |  |
| mRNA | 5' | CUG | ACU | CCU | GUG | GAG | AAG | UCU | GCC3' |  |  |  |
| H 19S' |  | 3' | GA | GGA | CAC | CTC | TTC | AGA | CG 5' | A:A | — | C:A+A:A |
| β$^C$ | ... |  | Leu | Thr | Pro | Lys | Glu | Lys | Ser | Ala ... |  |  |  |
| mRNA | 5' | CUG | ACU | CCU | AAG | GAG | AAG | UCU | GCC3' |  |  |  |
| H 19C' |  | 3' | GA | GGA | TTC | CTC | TTC | AGA | CG 5' | T:G | T:G+T:U | — |

$^{a/}$The codon affected by the mutation is underlined.

The position and length of the sequences is based on several considerations:

(1) The length of 19 nucleotide has been previously shown to give a probe that recognizes a unique sequence in the human genome. See Connor, et al., *Proc. Natl. Acad. Sci. USA* 80:278–282 (1983).

(2) The mismatches are centrally located to optimize thermal destablization.

(3) All sequences are anti-sense and are thus complementary to the MRNA.

(4) Each oligo is complementary to one allele of the β-globin gene and forms either one or two mismatches with the other alleles. Hβ19A' is specific for the β$^A$ allele, Hβ19S' for the β$^S$ allele and Hβ19C' for the B$^C$ allele.

Probe Labeling—The three 19-nucleotide oligos Hβ19A', Hβ19S' and Hβ19C' (see Table I) were synthesized on a Systec Microsyn 1450 automated DNA synthesizer. The oligos were radiolabeled at their 5'-ends using (γ-$^{32}$P]ATP and T4 polynucleotide kinase and purified by electrophoresis on a 19.35% acrylamide, 0.65% bisacrylamide, 7M urea gel.

Gel Electrophoresis and Blotting—RNA was denatured by dissolving in 6M glyoxal and 50% dimethyl sulfoxide and heating at 50° C. for 60 min. The denatured RNA was subjected to electrophoresis in a 1.5% agarose gel using 0.01M sodium phosphate pH 7 buffer. Electrophoresis was at 3.5 V/cm for 3 h. RNA was transferred to GeneScreen (New England Nuclear) by capillary blotting using 20×SSC buffer. The blots were dried at room temperature and baked in vacuo at 80° C. for 2 h.

Hybridization—The blots were prehybridized in 10× Denhardt's solution (0.2% bovine serum albumin, 0.2% polyvinylpyrrolidone and 0.2% Ficoll) and 0.1% SDS for 1 h at 60° C. The blots were then washed in 2×SSC and hybridized with the labeled oligo (1×10$^6$ cpm/ml) in 5×Denhardt's, 5×SSPE and 0.1% SDS for 3 h at 60° C. (58° C. in the case of Hβ19C'). For the hybridizations where unlabeled competitor oligo is included, it is added in a 10-fold molar excess over the labeled one. After hybridization the filters were washed three times with 6×SSC at room temperature for 15 min followed by one wash with 6×SSC at 57° C. for one min. The filter is then exposed to Kodak XAR X-ray film with two Dupont Quantum III intensifier screens at −70° C. for 0.5–3 h.

Effect of G:T Mismatch—To decrease the hybridization of non-c-oligos forming a G:T mismatch to the non-complementary target sequence, hybridizations were attempted using labeled c-oligo in the presence of a 10-fold molar excess of unlabeled non-c-oligo. The presence of the competitor oligo effectively suppressed any hybridization of the labeled oligo to its non-complementary target sequence.

FIG. 1 shows the effect of having the competitor oligo present during hybridization. mRNA was isolated from blood cells of individuals which were either homozygous for the normal β-globin gene (AA) or heterozygous for the normal and β$^C$ allele (AC). The RNA was glyoxylated in the presence of dimethylsulfoxide (DMSO), subjected to electrophoresis on an agarose gel and transferred to GeneScreen. Duplicate Northern blots containing the two RNAs were hybridized with [$^{32}$P]Hβ19C' in the absence (FIG. 1A) or presence (FIG. 1B) of a 10-fold molar excess of unlabeled Hβ19A'. In both cases, the Hβ19C' probe hybridizes strongly with the β-globin mRNA present in the AC RNA. In the absence of the competitor however, there was a low level of binding of the Hβ19C' probe to the normal β-globin RNA in the AA sample. This residual hybridization could only be reduced by long high-criteria washes (65° C. in 6×SSC) which also resulted in the loss of signal from the AC lane. In the presence of non-c-oligo competitor (FIG. 1B), there is essentially no binding of the Hβ19C' oligo to the β$^A$-globin mRNA.

Figure 2:
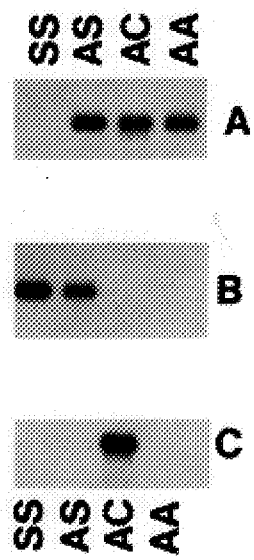
FIGS. 2(A–C) Discrimination among the transcripts of the allelic globin genes $β^A$, $β^S$ and $β^C$ by oligo hybridization. RNA was isolated from blood cells of individuals with the genotypes SS, AS, AC and AA. The RNA was denatured, electrophoresed and blotted as described in FIG. 1. The filter was hybridized sequentially as follows.

Specific Hybridization of Allele-Specific Probes to B$^A$, B$^S$ and B$^C$ mRNA—RNA was isolated from the blood cells of individuals with the following β-globin genotypes: AA, AC, AS and SS. The total RNA was denatured, subjected to electrophoresis and blotted onto a GeneScreen filter as described for FIG. 1. The blot containing the four RNA samples was hybridized first with Hβ19A'[$^{32}$P ]probe in the absence of unlabeled non-c-oligo (FIG. 2A). After the hybridized probe was removed, the filter was rehybridized with Hβ19S'[$^{32}$P]probe in the presence of unlabeled Hβ19A' oligo (FIG. 2B). The hybridized probe was once more removed and the filter was again rehybridized with Hβ19C' [$^{32}$P]probe in the presence of unlabeled Hβ19A' oligo (FIG. 2C). As can be seen, each probe only hybridized to RNA samples containing the homologous β-globin mRNA and not to samples containing non-homologous allelic transcripts. Thus, the allele-specific oligo probe can unambiguously distinguish among the transcripts of allelic genes both in the case where the genes differ by a single tranversion mutation as for $\beta^A$ vs. $\beta^S$ (compare the SS, AS and AA lanes in FIGS. 2A and 2B) as well as in the case where the genes differ by a single transition mutation as for $\beta^A$ vs. $\beta^C$ (compare the AC and AA lanes in FIGS. 2A and 2C).

We claim:

1. A hybridization assay for discriminating between first and second nucleic acid molecules, said first nucleic acid molecule including a target nucleotide sequence and said second nucleic acid molecule including a mutant sequence which differs by as little as one nucleotide from said target nucleotide sequence, which comprises:

subjecting a biological sample suspected of containing at least one of said first and second nucleic acid molecules to hybridization conditions in the presence of first and second oligonucleotide probes, said first oligonucleotide probe including a sequence complementary to said target sequence of said first nucleic acid molecule, said second oligonucleotide probe being non-complementary to said target sequence but complementary to said mutant sequence, said second probe being present in substantial excess during said hybridization to suppress hybridization of said first probe to said second nucleic acid molecule.

2. An assay in accordance with claim 1, wherein the nucleic acid is DNA.

3. A hybridization assay for discriminating between nucleic acid sequences present in two closely related genes and which differ by as little as one base pair which comprises:

subjecting nucleic acid sequences from said two closely related genes to hybridization conditions in the presence of at least first labeled and second unlabeled oligonucleotide probes, the sequence of said first, labeled oligonucleotide probe being such that a duplex with no mismatches is formed with the nucleic acid sequence of one of said genes and that duplexes, if any, formed with the nucleic acid sequence of the second of said genes includes mismatches, the sequence of the second, unlabeled oligonucleotide probe being such that a duplex with no mismatches is formed with the nucleic acid sequence of the second of said genes and that duplexes, if any, formed with the nucleic acid sequence of the said one of said genes includes mismatches, and said second, unlabeled probe being present in substantial molar excess in said hybridization reaction to suppress hybridization of said first, labeled probe to the nucleic acid of said second gene.

4. An assay in accordance with claim 3, in which the probes are about 19 nucleotides in length.

5. An assay in accordance with claim 3, wherein said nucleic acid sequences are DNA.

6. A method for discriminating between two nucleic acid molecules which differ by as little as a single nucleotide which comprises subjecting a biological sample suspected of containing at least one of said two nucleic acid molecules to hybridization conditions sequentially with first and second oligodeoxynucleotide probes said first probe, under said hybridization conditions forming a stable duplex with no mismatches with one of said two nucleic acid molecules and, in the absence of said second probe, a less stable duplex having at least a single mismatch with the other of said two nucleic acid molecules, said second probe, under said hybridization conditions, forming a stable duplex with no mismatches with said other of said two DNA molecules and a less stable duplex with said one of said nucleic acid molecules, and enhancing the instability of said less stable duplex formed between said first probe and said other of said two nucleic acid molecules by including an excess of said second probe in said hybridization reaction mixture.

7. A method in accordance with claim 6, wherein said nucleic acid molecules are DNA.

8. A hybridization assay for discriminating between first and second nucleic acid molecules, said first nucleic acid molecule including a target nucleotide sequence and said second nucleic acid molecule including a mutant sequence which differs by one nucleotide from said target nucleotide sequence which comprises:

subjecting a biological sample suspected of containing at least one of first and second nucleic acid molecules to hybridization conditions in the presence of first and second oligonucleotide probes, said first oligonucleotide probe including a sequence complementary to said target sequence of said first nucleic acid molecule, said second oligonucleotide probe being non-complementary to said target sequence but complementary to said mutant sequence, said second probe being present in substantial excess during said hybridization to suppress hybridization of said first probe to said second nucleic acid molecule.

9. A hybridization assay for discriminating between nucleic acid sequences present in two closely related genes and which differ by a single base pair which comprises:

subjecting nucleic acid sequences from said two closely related genes to hybridization conditions in the presence of at least first labeled and second unlabeled oligonucleotide probes, the sequence of said first, labeled oligonucleotide probe being such that a duplex with no mismatches is formed with the nucleic acid sequence of one of said genes and that duplexes, if any, formed with the nucleic acid sequence of the second of said genes includes mismatches, the sequence of the second, unlabeled oligonucleotide probe being such that a duplex with no mismatches is formed with the nucleic acid sequence of the second of said genes and that duplexes, if any, formed with the nucleic acid sequence of the said one of said genes includes mismatches, and said second, unlabeled probe being present in substantial molar excess in said hybridization reaction to suppress hybridization of said first, labeled probe to the nucleic acid of said second gene.

10. A method for discriminating between two nucleic acid molecules which differ by a single nucleotide which comprises subjecting a biological sample suspected of containing at least one of said two nucleic acid molecules to hybridization conditions sequentially with first and second, oligodeoxynucleotide probes said first probe, under said hybridization conditions forming a stable duplex with no mismatches with one of said two nucleic acid molecules and, in the absence of said second probe, a less stable duplex having at least a single mismatch with the other of said two nucleic acid molecules, said second probe, under said hybridization conditions, forming a stable duplex with no mismatches with said other of said two DNA molecules and a less stable duplex with said one of said nucleic acid molecules, and enhancing the instability of said less stable duplex formed between said first probe and said other of said two nucleic acid molecules by including an excess of said second probe in said hybridization reaction mixture.

\* \* \* \* \*